(12) United States Patent
Braeuer

(10) Patent No.: US 12,708,502 B2
(45) Date of Patent: Aug. 18, 2026

(54) STENT GRAFT AND KIT

(71) Applicant: Angiomed GmbH & Co. Medizintechnik KG, Karlsruhe (DE)

(72) Inventor: Pia U. Braeuer, Königsbach-Stein (DE)

(73) Assignee: Angiomed GmbH & Co. Medizintechnik KG, Karlsruhe (DE)

( * ) Notice: Subject to any disclaimer, the term of this patent is extended or adjusted under 35 U.S.C. 154(b) by 837 days.

(21) Appl. No.: 17/794,067

(22) PCT Filed: Jan. 20, 2020

(86) PCT No.: PCT/EP2020/051236
§ 371 (c)(1),
(2) Date: Jul. 20, 2022

(87) PCT Pub. No.: WO2021/148105
PCT Pub. Date: Jul. 29, 2021

(65) Prior Publication Data
US 2023/0050140 A1 Feb. 16, 2023

(51) Int. Cl.
*A61F 2/07* (2013.01)
*A61B 17/06* (2006.01)
(Continued)

(52) U.S. Cl.
CPC ........ *A61F 2/07* (2013.01); *A61F 2210/0061* (2013.01); *A61F 2210/0076* (2013.01); *A61F 2230/0065* (2013.01)

(58) Field of Classification Search
None
See application file for complete search history.

(56) References Cited

U.S. PATENT DOCUMENTS 5,197,978 A 3/1993 Hess
5,735,897 A * 4/1998 Buirge .................. A61M 29/02
623/1.42
(Continued)

FOREIGN PATENT DOCUMENTS

FR 2929525 A1 * 10/2009 .......... A61M 60/268
WO WO-9840033 A2 * 9/1998 ......... A61K 47/6957
(Continued)

OTHER PUBLICATIONS

Conatex Lernsysteme, "Osmose Diffusion Kit" https://www.conatex.com/catalog/biologie_lehrmittel/biochemie/biomembranen_osmose/product-diffusion_osmose_kit_klassensatz/sku-1086419#.Y0RvinbMJaR, last accessed Oct. 10, 2022.
(Continued)

*Primary Examiner* — Ann Hu
(74) *Attorney, Agent, or Firm* — Rutan & Tucker LLP

(57) ABSTRACT

The present invention relates to a stent graft, comprising: a hollow stent graft body having a lumen extending from one end of the stent graft body to the respective other end of the stent graft body, an expandable reservoir provided on an interior of the stent graft body, the expandable reservoir being covered with a separation layer on a side of the expandable reservoir facing the lumen, the expandable reservoir being arranged so as to swell when exposed to blood, the separation layer being arranged to prevent the expandable reservoir from being exposed to blood flowing through the lumen, the separation layer being arranged so that it can selectively expose the expandable reservoir to blood to cause the expandable reservoir to swell.

15 Claims, 2 Drawing Sheets

(51) Int. Cl.
*A61M 1/12* (2006.01)
*A61M 60/135* (2021.01)

(56) References Cited

U.S. PATENT DOCUMENTS

| | | | | |
|---|---|---|---|---|
| 5,755,779 | A | 5/1998 | Horiguchi | |
| 5,899,917 | A * | 5/1999 | Edwards | A61L 31/18 606/195 |
| 6,120,534 | A | 9/2000 | Ruiz | |
| 7,211,108 | B2 * | 5/2007 | Furst | A61F 2/06 428/36.9 |
| 8,034,046 | B2 * | 10/2011 | Eidenschink | B29C 70/882 604/523 |
| 11,253,690 | B2 * | 2/2022 | Judisch | A61M 60/454 |
| 2002/0049491 | A1 | 4/2002 | Yassour | |
| 2002/0082680 | A1 * | 6/2002 | Shanley | A61F 2/91 623/1.42 |
| 2004/0086542 | A1 * | 5/2004 | Hossainy | A61L 29/085 427/2.28 |
| 2004/0202692 | A1 * | 10/2004 | Shanley | A61M 25/007 424/426 |
| 2004/0225346 | A1 * | 11/2004 | Mazumder | A61F 2/90 623/1.13 |
| 2005/0171556 | A1 * | 8/2005 | Murphy | A61B 17/1219 606/108 |
| 2009/0198216 | A1 * | 8/2009 | Muni | A61F 11/20 604/514 |
| 2010/0028403 | A1 * | 2/2010 | Scheuermann | A61L 31/16 424/423 |
| 2011/0060398 | A1 | 3/2011 | Tupil et al. | |
| 2015/0051694 | A1 | 2/2015 | Furey | |
| 2018/0085128 | A1 | 3/2018 | Bellomo et al. | |

FOREIGN PATENT DOCUMENTS

| | | | | |
|---|---|---|---|---|
| WO | WO-2007038476 | A2 * | 4/2007 | A61F 2/95 |
| WO | WO-2019241414 | A1 * | 12/2019 | A61F 2/04 |

OTHER PUBLICATIONS

Pasparakis, G., et al., "Photodegradable Polymers for Biotechnological Applications" Macro-molecular rapid communications vol. 33, Iss. 3, pp. 183-198, Feb. 13, 2012.

Yang, S. et al., "Visible-light degradable polymer coated hollow mesoporous silica nanoparticles for controlled drug release and cell imaging." Journal of Materials Chemistry B, Issue 36, 2013.

* cited by examiner

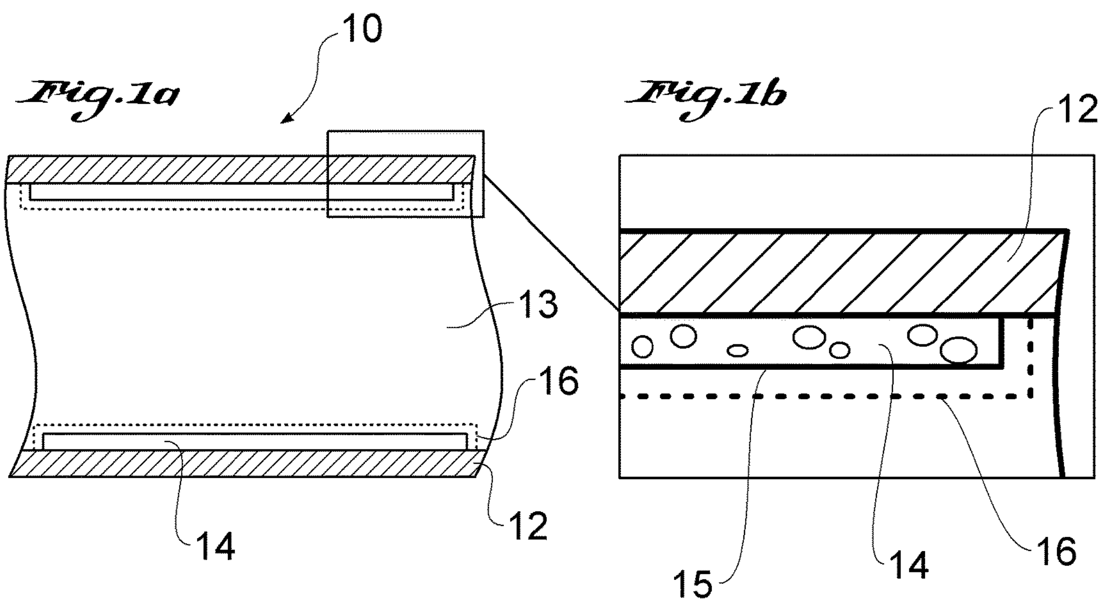
Fig.1a
10
13
16
12
14
Fig.1b
12
15
14
16
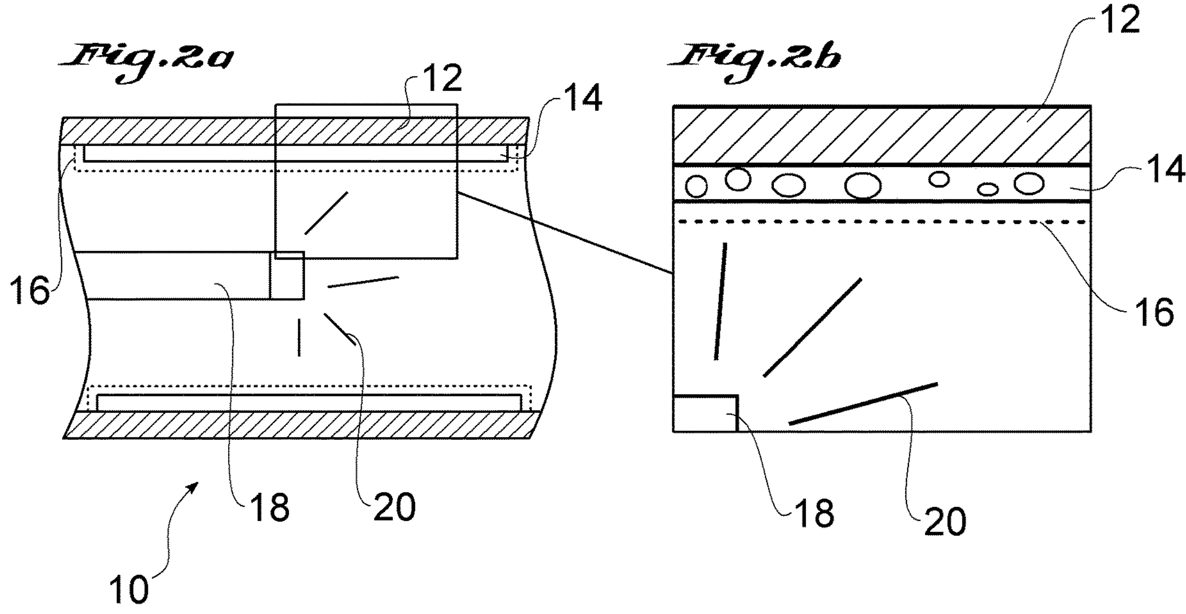
Fig.2a
12
14
16
18
20
10
Fig.2b
12
14
16
18
20

Fig.3
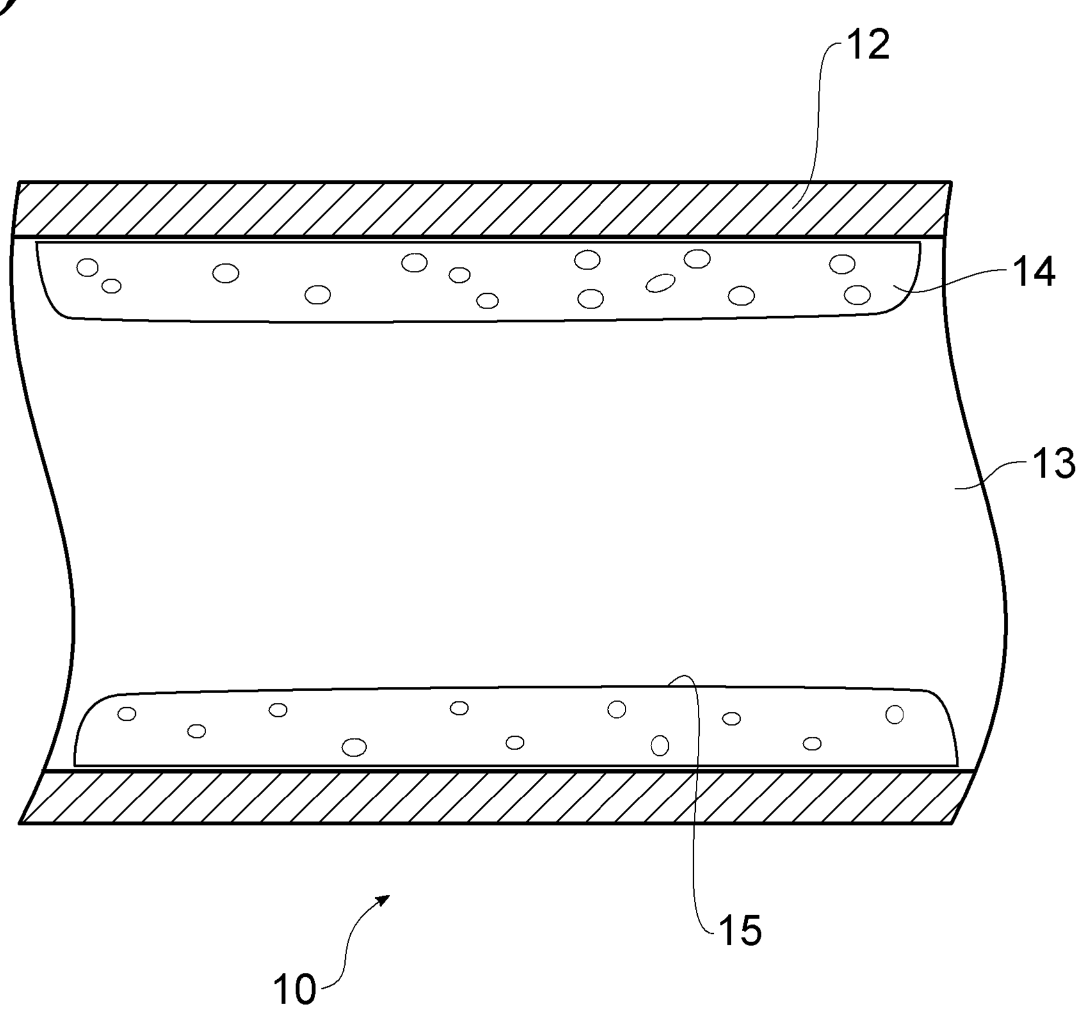
12
14
13
15
10

STENT GRAFT AND KIT

PRIORITY

This application is a U.S. national stage application of International Application No. PCT/EP2020/051236, filed Jan. 20, 2020, which is incorporated by reference in its entirety into this application.

TECHNICAL FIELD

The present invention relates to stent grafts that may be for use as transjugular intrahepatic portosystemic shunts (TIPS) and a kit comprising such a stent graft.

TECHNICAL BACKGROUND

Portal hypertension is an increase in the pressure in the digestive organ venous vasculature system that is returning venous blood through the liver and eventually to the heart but which is obstructed due to a diseased liver condition (such as a liver cirrhosis). When untreated, it frequently leads to intestinal bleeding or potentially life threatening oesophageal bleeding. Other complications could be the formation of excessive venous vessel expansion ("varices"), which can leads to sudden bleeding and death, or ascites with water accumulation in the peritoneum.

A transjugular intrahepatic portosystemic shunt (TIPS) is used to address portal hypertension and its complications. The shunt which is made of a TIPS stent graft, i.e., a covered stent, extends through an artificial channel created within the liver and re-roots venous blood from the portal vein to the hepatic vein to reduce the pressure gradient across the liver.

However, post TIPS placement, 20% to 30% of the patients suffer hepatic encephalopathy due to an overly high venous flow bypassing the liver through the shunt. This is because a smaller proportion of the blood is filtered due to a significant amount of blood bypassing the liver, so that a high volume of unfiltered blood and toxic molecules enters the brain. The thus caused hepatic encephalopathy goes along with neuropsychiatric abnormalities characterised by personality changes, intellectual impairment, and a depressed level of consciousness.

Further, there is a poor patient survival. The occurrence of hepatic encephalopathy leads to hospitalisation and is associated with a survival probability of about 42% over one year and 23% over 3 years. Given that hepatic encephalopathy is caused by the blood flow through the TIPS being excessively high, a need exists for a TIPS which can be reduced in its diameter post-placement.

Commercially available TIPS stent grafts have the ability to be increased from an initial diameter of about 8 mm to a diameter of about 10 mm to optimise the portal pressure at the time of placement. However, not all devices have the ability to be adjusted in their diameter after placement and, in particular, currently available devices cannot be restricted in their diameter post-placement.

Further, it has become known in the medical community that TIPS shunts can increase their diameter over time and thus allow a later increase of the blood flow. Also this behaviour has the potential to cause or exacerbate hepatic encephalopathy.

Accordingly, there is a need to provide a TIPS stent graft which can be reduced in its diameter post-placement. Also in other circumstances, stent grafts that can be reduced in their diameter are desirable.

SUMMARY OF THE INVENTION

The present invention aims to solve the problems mentioned above and aims at providing a stent graft, in particular a TIPS stent graft, which can be reduced in its diameter post-placement.

According to one embodiment, a stent graft that can be for use in a TIPS procedure comprises a hollow stent graft body formed by a covered stent. The stent can be a self-expanding stent and could, for example, be made of nitinol. The stent is covered by a suitable covering material (for example expanded polytetrafluoroethylene ("ePTFE")) and thus creates a hollow tube. In certain embodiments, the stent of the TIPS stent grafts is bare (i.e. there is no covering material covering the stent at that point). This uncovered portion can serve to anchor the TIPS stent graft in the portal vein.

This stent graft body comprises a lumen extending from one longitudinal end of the stent graft body to the respective other longitudinal end of the stent graft body. The lumen can serve for allowing a liquid to flow from one end of the stent graft body to the respective other end of this stent graft body.

According to an aspect of the invention, an expandable reservoir is provided on an interior of the stent graft body. I.e., that expandable reservoir is provided so as to face the lumen. The expandable reservoir is covered with a separation layer on a side of the expandable reservoir facing the lumen so as to separate the expandable reservoir from any liquid flowing through that lumen. The expandable reservoir is arranged so as to swell when exposed to blood. This could be due to it containing an osmotically active substance which should also be biocompatible. For example, sugar molecules of appropriate size (that is, sugar having molecules that are significantly larger than water molecules) as are used in dialysis could be used as the osmotically active substance.

The separation layer is arranged to prevent the expandable reservoir from being exposed to blood flowing through the lumen. I.e., it is this separation layer which prevents the expandable reservoir from swelling when exposed to blood. This separation layer should be impenetrable and insoluble in blood so that it will not expose the expandable reservoir to blood unless desired by a clinician.

The separation layer is arranged so that it can selectively expose the expandable reservoir to blood to cause the expandable reservoir to swell. When the separation layer exposes the expandable reservoir to blood, components of the blood such as the blood plasma or the water will seep into the expandable reservoir to cause it to expand. This will, in turn, reduce the cross-sectional area of the lumen. Accordingly, the stent graft is capable of being reduced in its inner diameter post-placement.

In some embodiments, there is a semipermeable membrane between the expandable reservoir and the separation, where the membrane is made of a different material from the expandable reservoir. Such a membrane can be made e.g. of polysulfone, polyethersulfone, polyarylethersulfone, polyamide, polyvinylpyrolidone, polycarbonate, polyacrylonitrile or cellulose acetate, or modified cellulose having pore sizes that allow water molecules to pass therethrough but do not allow for passage of the molecules of the osmotically active substance. Such semipermeable membranes allow water molecules to pass therethrough but do not allow for the passage of sugar or other, larger molecules. Such a semipermeable membrane is good in retaining the material of the expandable reservoir—i.e., it ensures that the material such as the osmotic substance of the expandable reservoir is retained in its position close to the walls of the stent graft. It thus ensures that the expandable reservoir retains its shape.

In some embodiments, the separation layer is arranged to expose the expandable reservoir to blood when exposed to light of a pre-set wavelength. By doing so, in particular by using a separation layer which will disintegrate when exposed to light of a certain pre-set wavelength, it becomes easy to expose the expandable reservoir to blood, namely by introducing a catheter comprising an optical fibre conducting light of that wavelength into the placed stent graft and then shining appropriate light through that optical fibre onto the separation layer. Such a separation layer could be made of an amphiphilic copolymer, which degrades when exposed to light having a wavelength of from 500 to 540 nm. Suitable materials include homo- and blockcopolymers of polyacrylates, polytriazenes, and polyketals. E.g. thin films of vinyl ketone based block polymers synthesized with polystyrene have a photodegradability at 366 nm, and PEGMA polymer brush substrate is photodegradable at 400 nm. Further details can be found in G. Pasparakis et al., "Photodegradable Polymers for Biotechnological Applications", Macromol. Rapid Commun. 2012, 33, 183-198.

In some embodiments, the separation layer is arranged to become permeable to blood when exposed to one or suitable chemicals. Such stent grafts can be easily implemented and can have the separation layer easily dissolved, namely simply by exposing it to the right drugs. For example, one could introduce into the patient's vasculature a catheter coated with those drugs or one could, alternatively, inject those drugs into a patient's vasculature without having to rely on a catheter.

In embodiments, the expandable reservoir is formed as a ring surrounding the lumen. This leads to a homogenous reduction in diameter when the expandable reservoir expands.

In some embodiments, the stent graft comprises a plurality of separate expandable reservoirs which are arranged at different axial positions inside the stent graft body. Having such a configuration gives more flexibility in the design and also allows for, if need be, only expanding some reservoirs but not all of them. This gives more flexible in reducing the cross-sectional diameter of the stent graft.

According to another aspect of the invention, the invention relates to a kit of parts which comprises the stent graft as defined previously and a catheter arranged to cause a separation layer to expose the expandable reservoir to blood, thereby allowing it to swell.

In some embodiments, the kit of parts comprises the stent graft having a separation layer which is arranged to expose the expandable reservoir to blood when exposed to light of a pre-set wavelength, together with a catheter comprising an optical fibre are arranged to conduct light from a proximal end of the catheter to a distal end of the catheter to then exit the catheter—i.e., the light leaves from the distal end of the catheter. The kit of parts further comprises a light source arranged to emit light of the pre-set wavelengths which can thus cause the separation layer to disintegrate. Using such as kit of parts, the stent graft can, if desired, be easily caused to be reduced in its diameter even after implantation.

In some embodiments, the kits of parts comprises the stent graft with a separation layer, and a catheter being arranged to release one or more appropriate chemicals. By releasing such chemicals, one causes the separation layer to disintegrate to thus become permeable to at least certain components of blood so that the expandable reservoir can swell.

BRIEF DESCRIPTION OF THE DRAWINGS

FIG. 1 shows schematically a cross-section of a TIPS stent graft according to the first embodiment of the invention.

FIG. 2 shows a way in which the stent graft according to the embodiment can be used.

FIG. 3 shows the stent graft of the embodiment of the invention in the expanded state.

DETAILED DESCRIPTION OF THE DRAWINGS

FIG. 1*a*) shows a cross-sectional view of a TIPS stent graft 10 according to the present invention. Whilst not shown, one of the longitudinal ends of the stent graft 10 has a bare stent, i.e. that end has no covering material for the stent underlying the stent graft 10.

The stent graft 10 comprises a stent graft body 12 having a hollow tubular shape. The stent graft body 12, i.e. the body of the TIPS stent, surrounds a lumen 13 by which a fluid can flow through the stent graft 10. On the inside of the stent graft body 12, an expandable reservoir 14 which is covered first by a semipermeable membrane 15 and then by a separation layer 16 is provided, as is shown in more detail in FIG. 1*b*). The expandable reservoir 14 comprises an osmotically active substance. The separation layer 16 is permeable to blood or some of its components but does not let the material of the expandable reservoir 14 through and therefore keeps that material in place. The semipermeable membrane 15 is permeable to blood or at least some of its components but is impermeable to the material of the expandable reservoir 14. Accordingly, when the separation layer 16 is made permeable to blood, the expandable reservoir 14 will swell.

The stent graft 10 as shown in FIGS. 1*a*), *b*) is implanted in a patient's body. If some time after placement, it is desired to further restrain the diameter of the TIPS stent graft 10, the procedure shown in FIGS. 2*a*), *b*) can be performed. A catheter 18 is introduced into the patient's vasculature which comprises an optical fibre (not shown). Through this optical fibre, light 20, such as ultraviolet light, can be shone onto the surface of the separation layer 16 to disintegrate it whilst the semipermeable membrane 15 remains unaffected by the light. Accordingly, the expandable reservoir 14 is exposed to blood flowing through the lumen 13.

As can be seen in FIG. 3, due to the liquid present in the blood, the reservoir 14 expands, as can be seen from FIG. 3. This expansion reduces the volume available in the lumen 13 for blood to flow through. Accordingly, the stent graft 10 is capable of, if desired, reducing its inner diameter.

Whilst in the present embodiment, a situation was described where the separation layer 16 is made permeable by light, it is also possible to make this layer permeable by exposing it to appropriate drugs. Further, it is also conceivable to implement a mechanism to mechanically fracture the separation layer 16, for example by having threads implanted into it which can be pulled out and which will, when pulled out, rip apart the separation layer 16. If one wants to use a separation layer 16 which can be made permeable by means of a chemical reaction, one can use a catheter with PTA balloon which is coated with the appropriate chemicals. Once the balloon has been placed inside the stent graft, it can then be expanded to be brought into contact with the separation layer 16. By that contact, the separation layer 16 will be caused to become permeable, so that the expandable reservoir can swell.

The invention claimed is:

1. A stent graft, comprising:

a hollow stent graft body having a lumen extending from one end of the hollow stent graft body to a second end of the hollow stent graft body;

an expandable reservoir provided within the lumen of the hollow stent graft body, the expandable reservoir being covered with a separation layer on a side of the expandable reservoir exposed to the lumen, the expandable reservoir configured to swell when exposed to blood within the lumen, the separation layer initially configured to prevent the expandable reservoir from being exposed to the blood flowing through the lumen; and the separation layer being configured to selectively expose the expandable reservoir to the blood to cause the expandable reservoir to swell, wherein swelling of the expandable reservoir reduces a cross-sectional area of the lumen.

2. The stent graft according to claim 1, further comprising a semipermeable membrane between the expandable reservoir and the separation layer.

3. The stent graft according to claim 1, the separation layer being configured to expose the expandable reservoir to the blood when exposed to light of a pre-set wavelength.

4. The stent graft according to claim 1, the separation layer being configured to become permeable to the blood when exposed to one or more chemicals.

5. The stent graft according to claim 1, the expandable reservoir having a ring shape surrounding the lumen.

6. The stent graft according to claim 1, the stent graft comprising a plurality of expandable reservoirs, the plurality of expandable reservoirs being arranged at different axial positions inside the hollow stent graft body.

7. A kit of parts, comprising the stent graft according to claim 1, and a catheter configured to cause the separation layer to expose the expandable reservoir to the blood, thereby allowing it to swell.

8. The kit of parts according to claim 7, wherein the catheter comprises an optical fiber configured to conduct light from a proximal end of the catheter to a distal end of the catheter to thus exit the catheter, the kit of parts further comprising a light source configured to emit light of a pre-set wavelength, the optical fiber is configured to transmit the light to the distal end of the catheter.

9. The kit of parts according to claim 7, wherein the catheter is configured to release one or more appropriate chemicals selected so as to render the separation layer permeable to allow for the expandable reservoir to swell due to exposure to the blood.

10. A stent graft, comprising:

a hollow stent graft body having a lumen extending from a first end of the hollow stent graft body to a second end of the hollow stent graft body; and an expandable reservoir provided within the lumen of the hollow stent graft body, the expandable reservoir configured to swell when exposed to blood within the lumen, but covered with a separation layer on a side of the expandable reservoir facing the lumen to prevent the expandable reservoir from being exposed to the blood flowing through the lumen, wherein the separation layer is configured to selectively expose the expandable reservoir to the blood, wherein swelling of the expandable reservoir reduces a cross-sectional area of the lumen.

11. The stent graft according to claim 10, further comprising a semipermeable membrane between the expandable reservoir and the separation layer.

12. The stent graft according to claim 10, wherein the separation layer is configured to expose the expandable reservoir to the blood when exposed to light of a pre-set wavelength.

13. The stent graft according to claim 10, wherein the separation layer is configured to become permeable to the blood when exposed to one or more chemicals.

14. The stent graft according to claim 10, wherein the expandable reservoir includes a ring shape surrounding the lumen.

15. The stent graft according to claim 10, wherein the expandable reservoir comprises a plurality of separate expandable reservoirs arranged at different axial positions on an interior of the hollow stent graft body.

* * * * *